United States Patent
Shannon et al.

(10) Patent No.: US 6,267,834 B1
(45) Date of Patent: *Jul. 31, 2001

(54) PROCESS OF MANUFACTURING A RADIALLY EXPANDABLE PTFE TAPE-REINFORCED VASCULAR GRAFT

(75) Inventors: Donald Shannon, Mission Viejo; John McIntyre, Vista; Chris Kuo, Orange; Chris McCollam, Irvine; Robert Peterson, Dove Canyon, all of CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/201,953

(22) Filed: Dec. 1, 1998

Related U.S. Application Data (60) Continuation of application No. 08/844,482, filed on Apr. 18, 1997, now Pat. No. 5,843,173, which is a division of application No. 08/423,762, filed on Apr. 17, 1995, now Pat. No. 5,641,373.

(51) Int. Cl.[7] .................................................. B32B 31/26
(52) U.S. Cl. .......................... 156/84; 156/86; 156/242; 264/127; 264/230; 264/294; 264/342 R; 623/1.1; 623/1.25; 623/901; 606/194; 600/36
(58) Field of Search .............................. 156/84–86, 294, 156/303.1, 308.2, 242; 264/127, 230, 294, 342 R; 623/1.1, 1.12, 1.14, 1.23–1.25, 11.11, 901; 606/194–195, 198; 600/36; 128/898

(56) References Cited

U.S. PATENT DOCUMENTS

| | | | |
|---|---|---|---|
| 3,225,129 | * 12/1965 | Taylor et al. | 264/230 |
| 3,939,243 | * 2/1976 | Dawson | 264/296 |
| 4,909,979 | * 3/1990 | Possis et al. | 264/571 |
| 4,955,899 | * 9/1990 | Della Corna et al. | 623/1 |
| 4,957,669 | * 9/1990 | Primm | 264/23 |
| 5,026,513 | * 6/1991 | House et al. | 264/127 |
| 5,128,092 | * 7/1992 | Asaumi et al. | 264/544 |

* cited by examiner

Primary Examiner—Michael W. Ball
Assistant Examiner—Jessica Rossi
(74) Attorney, Agent, or Firm—Vascular Therapies Div.; Guy L. Cumberbatch; Peter Jon Gluck (57) ABSTRACT

A method for improving the radial enlargeability and other properties of tape-reinforced tubular vascular graft formed of sintered fluoropolymer(s), such as expanded, sintered PTFE. Broadly, the method comprises the step of radially shrinking the reinforcement tape layer of the graft, or the entire tape-reinforced graft, after sintering thereof. Such radial shrinkage of the reinforcement tape layer, or of the entire graft, renders the graft subsequently radially enlargeable by more than 5%, without tearing or breaking of the reinforcement tape layer of the graft. Radially enlargeable grafts of the present invention may be combined with various types of stents or anchoring systems, to form endovascular graft devices which are transluminally insertable and implantable within the lumen of a host blood vessel. Alternatively, radially enlargeable grafts of the present invention may be implanted by way of traditional surgical graft implantation techniques, without any radial enlargement of the graft at the time of implantation, so as to take advantage of the improved strength properties and suture-holding properties of the radially-shrunken tape-reinforced grafts of the present invention.

25 Claims, 3 Drawing Sheets

PROCESS OF MANUFACTURING A RADIALLY EXPANDABLE PTFE TAPE-REINFORCED VASCULAR GRAFT

This is a Continuation of application Ser. No. 08/844,482, filed Apr. 18, 1997, now U.S. Pat. No. 5,843,173, which is a divisional of U.S. Ser. No. 08/423,762, filed Apr. 17, 1995, now U.S. Pat. No. 5,641,373.

FIELD OF THE INVENTION

The present invention relates generally to bioprosthetic vascular grafts, and more particularly to a method of manufacturing radially enlargeable, tubular, tape-reinforced polytetrafluoroethylene (PTFE) vascular grafts.

BACKGROUND OF THE INVENTION

Polytetrafluoroethylene (PTFE) has been used for the manufacture of various types of bioprosthetic vascular grafts, including tape-reinforced, tubular grafts of the type frequently utilized to replace or bypass a diseased or injured segment of blood vessel.

The expanded sintered PTFE from which the tubular base graft and the surrounding reinforcement tape are formed typically has a microstructure characterized by the presence of dense areas known as "nodes" interconnected by elongate strands known as "fibrils". The directional orientation of fibrils is largely determined by the direction(s) in which the material was expanded prior to sintering thereof. The diameter and spacing of the fibrils is largely determined by the dynamics (i.e., rate frequency and amount) of the expansion. The porosity of the expanded sintered PTFE material is determined by the size of the spaces which exist between the fibrils, after the expansion step has been completed.

The sintering of the expanded PTFE is accomplished by heating the expanded workpiece to a temperature above the melting point of crystalline PTFE. Typically, this is effected by heating the workpiece to a temperature of 350°–370° C. This sintering process is characterized by a transition of the PTFE polymer from a highly crystalline form to a more amorphus form. Thus, the sintering process is sometimes referred to as "amorphous locking" of the PTFE polymer. The sintering process imparts significantly improved strength to the PTFE polymer matrix, while also causing the polymer matrix to become harder and less stretchable.

In the tape-reinforced PTFE vascular grafts of the prior art, it has been typical for the PTFE reinforcement tape to be wound spirally about the outer surface of the base graft. Such orientation and positioning of the relatively thin, sintered, PTFE reinforcement tape about the outer surface of the base graft substantially precludes or severely limits the amount of radial stretching or radial expansion that the base graft may undergo. Thus, the typical tape-reinforced tubular PTFE vascular graft of the prior art is incapable of undergoing more than a minimal amount (e.g., <5%) of radial stretching or radial expansion without tearing of the surrounding reinforcement tape.

The inability of tape-reinforced PTFE vascular grafts to undergo radial stretching or radial expansion has not interfered with the usual surgical implantation of such grafts because, in the usual surgical graft implantation procedure, the graft is sized-matched to the host blood vessel and is subsequently anastomosed into or onto the host blood vessel. Thus, in traditional surgical implantation procedures, there has been little or no need to effect radial stretching or radial expansion of the graft at the time of implantation.

Recently developed endovascular grafting procedures have, however, created a need for tape-reinforced tubular PTFE vascular grafts which are capable of undergoing significant amounts of radial enlargement (i.e., radial expansion with resultant enlargement of the radial dimension of the graft). In these endovascular grafting procedures, the tubular vascular graft is typically passed through a catheter into the lumen of a deceased blood vessel and, thereafter, is deployed to an open or extended configuration within the lumen of the host blood vessel. The graft is then anchored to the surrounding blood vessel wall, thereby effecting the desired endovascular placement of the graft within the lumen of the existing blood vessel. Thus, because it is necessary to initially compact the graft and pass it through the lumen of a relatively small catheter, and to subsequently radially enlarge the graft to its desired size and configuration, there exists a present need for the development of a tape-reinforced tubular vascular graft which is capable of undergoing in situ radial enlargement within the lumen of an existing blood vessel.

SUMMARY OF THE INVENTION

The present invention comprises a method for increasing or improving the ability of a tape-reinforced tubular graft (e.g., a graft comprising a tubular base graft formed of expanded sintered PTFE and a quantity of expanded sintered PTFE reinforcement tape wrapped about the outer surface of the base graft) to undergo radial enlargement without tearing or breaking.

In accordance with the present invention, a radially enlargeable tape-reinforced tubular vascular graft may be formed by initially manufacturing the tape-reinforced graft in accordance with any suitable manufacturing methodology, and subsequently radially shrinking the tape-reinforced graft to a decreased radial size. Such radial shrinkage of the tape-reinforced graft may be accomplished gradually, or in incremental steps, to minimize the likelihood of puckering of the tubular base graft as the surrounding reinforcement tape shrinks. Also, such radial shrinkage of the graft may be accomplished by any suitable polymer shrinkage technique, including heat-induced shrinkage or chemical-induced shrinkage.

Further in accordance with the present invention, one or more rigid mandrel(s) may be inserted into the lumen of the tubular base graft during the shrinkage process. In embodiments of the invention wherein the shrinkage process is accomplished in incremental or step wise manner, a single mandrel of adjustable diameter, or multiple mandrels of incrementally smaller diameter, may be utilized to effect the desired gradual, incremental or step-wise shrinkage of the graft.

Further in accordance with the invention, the desired shrinkage of the tape-reinforced graft may be accomplished by passing the tape-reinforced graft through a sizing dye to accomplish the desired radial shrinkage thereof.

Still further in accordance with the invention, the radially enlargeable tape-reinforced PTFE vascular graft may be alternatively formed by initially wrapping the expanded sintered PTFE reinforcement tape about the rigid mandrel to create a tape-tube which is devoid of any tubular base graft. The tape-tube is then radially shrunken, in accordance with the present invention, and the radially shrunken tape tube is subsequently applied to the outer surface of a relatively small-diameter tubular base graft. The tubular base graft and the surrounding shrunken tape-reinforcement may then be radially enlarged in accordance with the present invention, without tearing or breaking of the reinforcement tape.

Still further in accordance with the present invention, any embodiment of the radially enlargeable tape-reinforced tubular PTFE grafts of the present invention may be provided with external support filaments or beading to provide structural support to the graft, and to prevent indentation or kinking of the graft lumen when implanted. Such support filaments or beading may be formed of PTFE or any other suitable material.

Further objects and advantages of the invention will become apparent to those skilled in the art upon reading and understanding of the following detailed description, and consideration of the accompanying figures.

DETAILED DESCRIPTION OF THE PREFERRED EMBODIMENT

The following detailed description and the accompanying drawings to which it refers are provided for purposes of describing and illustrating the presently preferred embodiments of the invention, and are not intended to limit the scope of the invention in any way.

1. Method for Manufacturing a Radially Expandable Tape-Reinforced, PTFE Vascular Graft As shown in the block diagram of FIG. 1, the preferred method of manufacturing a tape-reinforced vascular graft of the present invention involves separate preparation of a) an expanded, sintered, tubular PTFE base graft and b) an expanded, sintered PTFE reinforcement tape.

Figure 1:
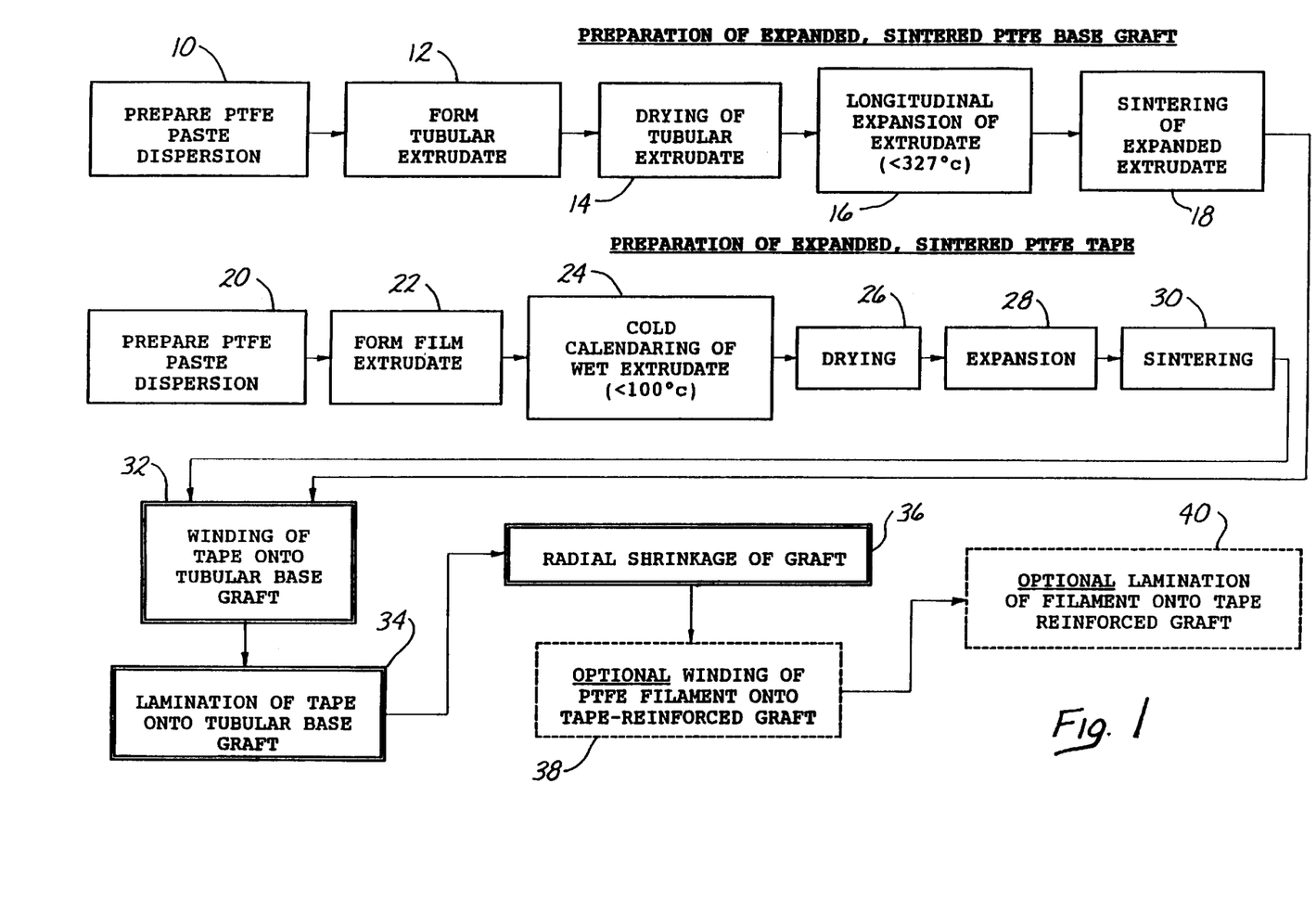
FIG. 1 is a block diagram showing a presently preferred method for manufacturing a radially enlargeable, tape-reinforced, tubular vascular graft of the present invention.

The PTFE reinforcement tape is then spirally wound about and laminated or fused to the outer surface of the tubular base graft, thereby forming the desired tape-reinforced vascular graft.

Thereafter, in accordance with the present invention, the sintered, tape-reinforced, tubular vascular graft is radially shrunken to a reduced radial dimension, such that the graft may be subsequently stretched or expanded to or near its original (pre-shrinkage) radial dimension.

A. Preparation of the Tubular Base Graft

The preferred method for preparing the expanded, sintered PTFE tubular base graft is shown in FIG. 1.

i.) Preparation of Paste

The manufacture of the tubular base graft begins with the step of preparing a PTFE paste dispersion 10 for subsequent extrusion. This PTFE paste dispersion may be prepared by known methodology whereby a fine, virgin PTFE powder (e.g., F-104 or F-103 Virgin PTFE Fine Powder, Dakin America, 20 Olympic Drive, Orangebury, N.Y. 10962) is blended with a liquid lubricant, such as odorless mineral spirits (e.g., Isopar®, Exxon Chemical Company, Houston, TX 77253-3272), to form a PTFE paste of the desired consistency.

ii.) Extrusion of Tube

The PTFE-lubricant blend dispersion is subsequently passed through a tubular extrusion dye to form a tubular extrudate 12. The extrudate formed in this step of the method has a diameter or cross-dimension which is approximately the same as the final diameter or cross-dimension desired of the graft after it has been implanted and subjected to in-situ radial expansion in accordance with the present invention.

iii.) Drying

The wet tubular extrudate is then subjected to a drying step 14 whereby the liquid lubricant is removed. This drying step 14 may be accomplished at room temperature or by placing the wet tubular extrudate in an oven maintained at an elevated temperature at or near the lubricants dry point for a sufficient period of time to result in evaporation of substantially all of the liquid lubricant.

iv.) Expansion

Thereafter, the dried tubular extrudate is longitudinally expanded 16 or longitudinally drawn at a temperature less than 327° C. and typically in the range of 250°–326° C. This longitudinal expansion 16 of the extrudate may be accomplished through the use of known methodology, and may be implemented by the use of a device known as a batch expander. Typically, the tubular extrudate is longitudinally expanded by an expansion ratio of more than two to one (2:1) (i.e., at least two (2) times its original length).

V.) Sintering

After the longitudinal expansion step has been completed, the tubular extrudate is subjected to a sintering step 18 whereby the extrudate is heated to a temperature above the sintering temperature of PTFE (i.e., 350°–370° C.) to effect amorphous-locking of the PTFE polymer. The methodology used to effect the sintering step, and the devices used to implement such methodology, are known in the art.

Completion of the sintering step 18, marks the completion of the preparation of the expanded, sintered PTFE base graft.

B. Preparation of Reinforcement Tape i.) Preparation of Paste Dispersion

In accordance with preferred method shown in FIG. 1, the preparation of the expanded sintered PTFE reinforcement tape includes the initial preparation of a PTFE paste dispersion 20. The PTFE paste dispersion prepared in this step 20 may be prepared in the same manner as described hereabove for preparation of the PTFE paste dispersion 10 used to form the tubular base graft.

ii.) Extrusion of Film

The PTFE paste dispersion 20 is subsequently passed through the film extrusion dye to form a wet film extrudate 22. The wet film extrudate is taken up or wound upon a rotating core so as to form a roll of the wet film extrudate.

iii.) Calendaring

The wet film extrudate is subsequently unrolled and subjected to an initial cold (i.e., <100° C.) calendaring step 24 by passing the film through at least one set of opposing stainless steel calendaring rollers having an adjustable gap thickness therebetween. The calendaring rollers are preferably maintained at a temperature between room temperature and 60° C. The width of the wet extrudate is held constant as it passes through these calendaring rollers. The thickness of the wet film extrudate is reduced to its desired final thickness (e.g., 0.004–0.005 inches) while the width of the film is maintained constant. It will be appreciated that, since the width of the film is maintained constant, the passage of the film through the calendaring machine will result in a longitudinal lengthening of the film. The amount of longitudinal lengthening will be a function of the decrease in film thickness which occurs as the film passes between the calendaring rollers.

One example of a commercially available calendaring machine useable for this purpose is the small Killion 2 Roll Stack, (Killion Extruders, Inc., Cedar Grove, N.J. 07009.)

iv) Drying

Thereafter, the wet film is subjected to a drying step 26. This drying step may be accomplished by permitting or causing the liquid lubricant to evaporate from the matrix of the film. Such evaporation of the liquid lubricant may be facilitated by passing the film over a drum or roller which is maintained in an elevated temperature sufficient to cause the liquid lubricant to fully evaporate from the film matrix.

v) Expansion

Separately, or concurrently with the drying step 26, the film is subjected to an expansion step 28. Such expansion step comprises expanding the PTFE film in at least one direction (e.g., longitudinally). Such expansion of the film serves to a) increase the porosity of the film, b) increase the strength of the film, and c) orient the PTFE fibrils in the direction of the axis of expansion.

This expansion step 28 is typically carried out with some heating of the film during such expansion, but such heating does not exceed the crystalline melting point of the PTFE polymer.

vi) Sintering

After the drying step 26 and expansion step 28 have been completed, the film is subjected to a sintering step 30 wherein the film is heated to a temperature above the melting point of PTFE to accomplish sintering or amorphous locking of the PTFE polymer. This sintering step 30 may be carried out by passing the film over a drum or roller which is maintained at a high surface temperature (e.g., 350°–420° C.) to cause the desired heating of the PTFE film above the melting point of the PTFE polymer for a sufficient period of time to effect the desired sintering of the film.

C. Wrapping and Lamination of the Reinforcement-Tape onto the Base Graft

After the sintered PTFE base graft and sintered PTFE reinforcement tape have been separately prepared, the tape-reinforced tubular graft is fabricated by spirally wrapping the PTFE reinforcement tape onto the outer surface of the tubular base graft 32. Thereafter, the tape is laminated or fused onto the outer surface of the graft 34.

Typically, in carrying out these steps (i.e., winding of the tape 32 and lamination 34 of the method, a first rigid stainless steel rod or mandrel, having an outer diameter substantially the same as the lumenal diameter of the sintered expanded tubular extrudate (i.e., the base graft) is inserted into the lumen of the base graft. Thereafter, the mandrel-borne sintered PTFE tubular base graft is rotated or spun about its longitudinal axis while the strips of expanded, sintered PTFE reinforcement tape are laid on the outer surface of the base graft, thereby spirally wrapping the tape onto the base graft to form the desired tape-reinforced graft structure. The ends of the tape reinforced graft are then affixed to the first mandrel by way of wire ligatures, thereby preventing the tape-reinforced graft from longitudinal shortening.

The mandrel-borne, tape-reinforced graft is then placed in an oven and heated to a temperature of approximately 355°–375° C. for a period of approximately 10–60 minutes to cause the sintered PTFE reinforcement tape to become laminated to the outer surface of the sintered PTFE base graft.

The presence of the first rigid mandrel within the lumen of the tape-reinforced graft prevents the tape-reinforced graft from undergoing radial shrinkage or contraction during this lamination step. Also, the wire ligatures affixing the ends of the tape-reinforced graft to the rigid mandrel prevent the graft from undergoing longitudinal shrinkage or shortening during this lamination step.

D. Radial Shrinkage of the Tape-Reinforced Graft

After the tape has been laminated onto the outer surface of the base graft to form the desired tape-reinforce graft structure, the tape-reinforced graft is subjected to radial shrinkage 36. This radial shrinkage step 36 may be carried out in one or more increments or stages.

In accordance with the preferred method, the radial shrinkage of the graft may be carried out by initially removing the wire ligatures which held the graft to the first rigid mandrel, and removing the first rigid mandrel from the lumen of the graft.

Thereafter, a second rigid mandrel, having an outer diameter which is smaller than the outer diameter of the first rigid mandrel, is inserted through the lumen of the graft, and the ends of the graft are affixed, by way of wire ligatures, to the second rigid mandrel.

Thereafter, the second rigid mandrel and the tape-reinforced graft disposed thereon are placed back in the oven at a temperature of 355° C. for a period of approximately 10 minutes to cause the graft to undergo radial shrinkage until the lumenal diameter of the graft has become substantially the same as the outer diameter of the second rigid mandrel.

Thereafter, the wire ligatures are removed and the second rigid mandrel is extracted from the lumen of the graft.

A third rigid mandrel, having an outer diameter which is smaller than the outer diameter of the second rigid mandrel, is then inserted through the lumen of the graft and wire ligatures are utilized to affix the ends of the graft to the third rigid mandrel.

Thereafter, the third rigid mandrel, along with the tape-reinforced graft disposed thereon, is placed in an oven at a temperature of 355° C. for a period of approximately 10 minutes to cause the graft to undergo further radial shrinkage until the lumenal diameter of the graft is substantially the same as the outer diameter of the third rigid mandrel.

The above-described shrinkage steps may be repeated consecutively using a number of progressively smaller rigid mandrels to effect incremental (e.g., staged) radial shrinkage of the graft. Care is taken to firmly affix the ends of the graft to each rigid mandrel prior to shrinkage thereof, so as to prevent the graft from undergoing longitudinal shrinkage or longitudinal shortening during the radial shrinkage process.

Although any suitable number of incremental shrinkage steps may be utilized, it is expected that in most applications the desired radial shrinkage of the graft will be accomplished with the use of no more than five (5) progressively smaller rigid mandrels.

For example, if it is desired to manufacture a tape-reinforced tubular graft which will have a lumenal diameter, when fully expanded, of 0.5 inches, it will be desirable to initially manufacture the tape-reinforced graft structure to have such 0.5 inch lumenal diameter prior to shrinkage thereof. Thereafter, the tape-reinforced graft structure may be subjected to incremental shrinkage of reduced diameter mandrels such as shown in the following example:

EXAMPLE

Preparation of A Radially Enlargeable Graft
Having an OD of 0.3 Inches

| MANDREL NO. | MANDREL OUTER DIAMETER |
| --- | --- |
| 1 | 0.5 inch |
| 2 | 0.45 inch |

-continued

Preparation of A Radially Enlargeable Graft
Having an OD of 0.3 Inches

| MANDREL NO. | MANDREL OUTER DIAMETER |
|---|---|
| 3 | 0.4 inch |
| 4 | 0.35 inch |
| 5 | 0.3 inch |

Thus, by incrementally shrinking the graft onto the outer surfaces of the five (5) shrinking mandrels listed hereabove, the lumenal diameter of the graft will be reduced from an initial lumenal diameter of 0.5 inches to a final lumenal diameter of 0.3 inches.

The tape-reinforced graft described hereabove, having a lumenal diameter of 0.3 inches, may then be re-expanded to a fully expanded diameter of approximately 0.5 inches—the same as its original diameter prior to shrinkage.

The incremental or step-wise shrinkage of the graft is for the purpose of preventing puckering or wrinkling of the graft as may occur if a large amount of radial shrinkage is effected in a single step. Although this incremental or step wise shrinkage is described hereabove with reference to a batch manufacturing method whereby individual segments of the graft material are placed on progressively smaller rigid mandrels or rods, it will be appreciated that the method of the present invention may also be carried out by various continuous techniques whereby the radial shrinkage of the graft will occur gradually, without puckering or wrinkling of the tubular base graft. For example, a continuous elongate tubular tape-reinforced graft may be drawn longitudinally over the surface of a gradually tapered or gradually narrowed rigid mandrel while heat is applied thereto to bring about the desired gradual radial shrinkage of the graft as it passes over the outer surface of the tapered or narrowed rigid mandrel. Alternatively, a segment of tape-reinforced tubular graft material may be initially placed on a single mandrel of adjustable or shrinkable diameter such that the mandrel will decrease or shrink in diameter as the graft shrinks in diameter.

It is intended that the present invention, as claimed herebelow, include any and all such continuous embodiments and/or adjustable/shrinkable mandrel embodiments of the method, as well as the specific batch-preparation method described hereabove. The radially shrunken tape-reinforced tubular PTFE grafts formed by the above-set-forth method may be cut into desired lengths, sterilized by gas or other suitable sterilization method(s), and packaged for distribution and subsequent implantation in a mammalian host.

It will be appreciated that the radially shrunken tape-reinforced PTFE vascular grafts of the present invention may be used in applications wherein they are anastomosed into a host blood vessel by known open surgical techniques, without being subjected to radial enlargement at the time of implantation of the graft. In these applications, one advantage which may be achieved through the use of the radially shrunken graft material is improved suture holding strength and a decreased likelihood of suture tear through when the ends of the graft are anastomosed to the host blood vessel.

Also, the radially shrunken tape-reinforced PTFE grafts of the present invention may be used in a variety of endovascular applications wherein they will be radially expanded or radially dilated at the time of implantation. In this regard, the radially expandable vascular grafts of the present invention may be used in conjunction with various presently known or hereafter invented anchoring devices, stents, or other support systems for affixing and holding the graft at its desired position within the lumen of a mammalian blood vessel.

F. Additional External Reinforcement

In some applications, it is desirable for the grafts manufactured by the method of the present invention to include an external reinforcement member, such as a PTFE filament wound spirally about and fused to the outer surface of the tape-reinforced graft. The type(s) of PTFE filaments used to form such reinforcement member are typically sufficiently stretchable to accommodate and undergo the desired amount of radial expansion or radial stretching of the tape-reinforced graft. Thus, it is possible to apply and affix such PTFE filament reinforcement member by traditional methods, after the tape-reinforced graft has been radially shrunk.

In accordance with the invention, in embodiments where it is desired to provide a PTFE reinforcement filament on the outer surface of the graft, the radially shrunken tape-reinforced graft provided at the end of the radial shrinkage step 36 may be positioned on a rigid mandrel having an outer diameter equal to the shrunken inner diameter of the graft lumen. Thereafter, a sintered PTFE monofilament bead, such as that commercially available as PTFE beading, (Zeus Industrial Products, Inc., Orangeburg, S.C.) is spirally wound about the outer surface of the tape-reinforced tubular graft 38.

Thereafter, the mandrel-borne tape-reinforced vascular graft having the PTFE filament spirally wound thereon is placed in an oven and heated to a temperature which is sufficient to fuse or laminate the PTFE reinforcement filament to the outer surface of the tape-reinforced graft 40.

It will be appreciated that alternative methods of fusing the beading to the outer surface of the graft may also be employed.

When so manufactured, the PTFE filament applied to the outer surface of the graft will undergo radial expansion or radial stretching concurrently with the remainder of the tape-reinforced graft prepared in accordance with the above-described method of the present invention.

2. Alternative Method for Forming the Radially Enlargeable Tape-Reinforced Graft As an alternative to the above-described method, wherein the entire tape-reinforced graft (i.e., the reinforcement tape in combination with the tubular base graft) is subjected to radial shrinkage, the radially expandable tape-reinforced graft of the present invention may also be manufactured by an alternative method wherein only the reinforcement tape is subjected to radial shrinkage, and such radially shrunken reinforcement tape is subsequently applied to a relatively small diameter tubular base graft such that the base graft-reinforcement tape combination is capable of subsequently undergoing radial enlargement without tearing or breaking of the reinforcement tape.

Figure 2:
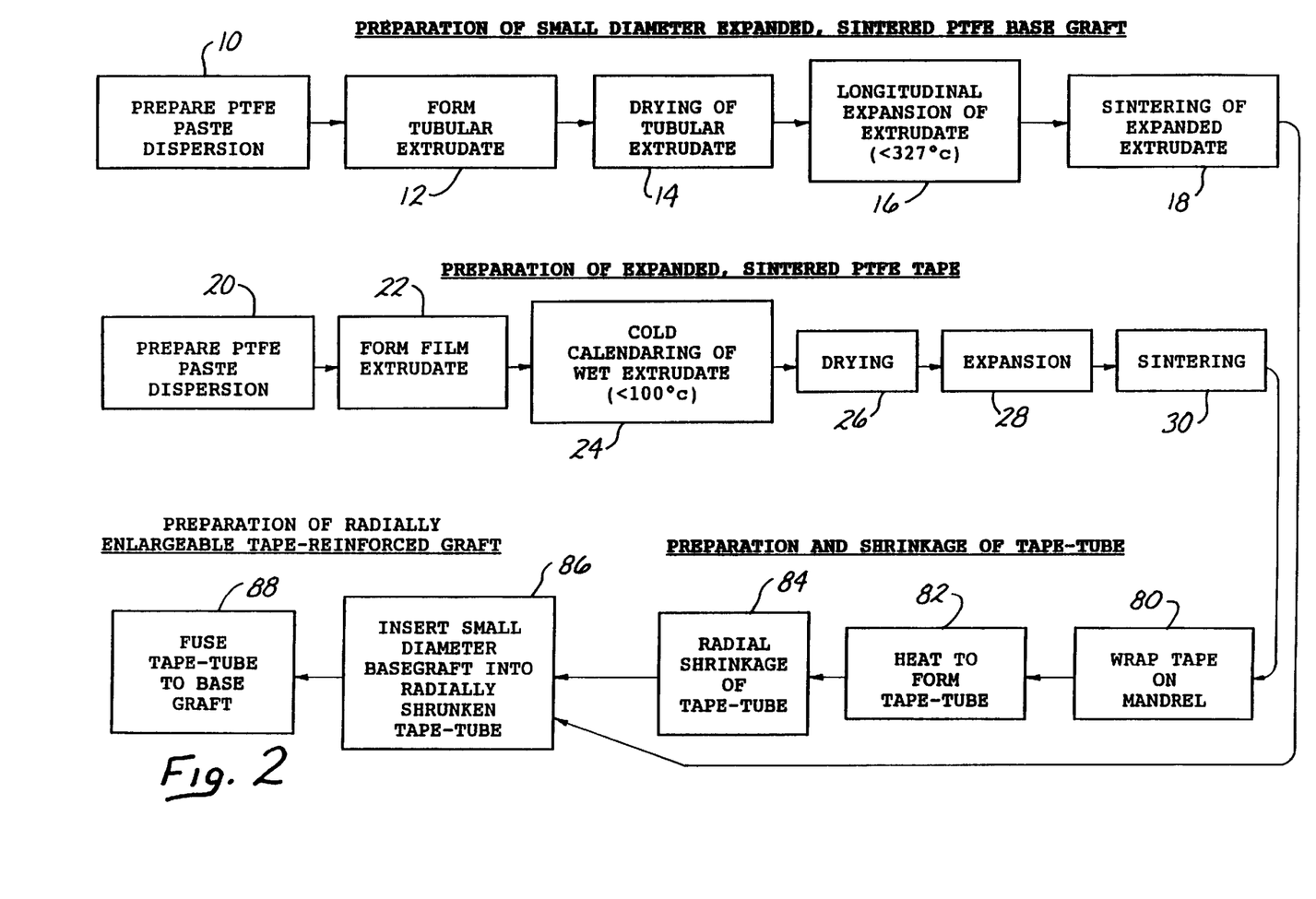
FIG. 2 is block diagram showing an alternative method for manufacturing a radially enlargeable tape-reinforced tubular vascular graft of the present invention.

This alternative method is shown in the block diagram of FIG. 2.

i. Preparation of Small Diameter Base Graft

A relatively small diameter tubular base graft is prepared of expanded sintered PTFE material by the same steps 10 through 18 as described hereabove. However, in this method, the tubular base graft is of a diameter which is equal to the desired diameter of the final tape-reinforced graft after radial shrinkage thereof. The tubular base graft is preferably a thin walled or ultra-thin walled graft capable of undergoing more than 5% radial enlargement without tearing or breaking.

ii) Preparation of PTFE Reinforcement Tape Tube

Also, in this method, a quantity of expanded sintered PTFE reinforcement tape is prepared by the same steps 20 through 30 as described hereabove. Thereafter, the expanded sintered PTFE reinforcement tape is used to prepare a "tape-tube" and such tape tube is subsequently subjected to radial shrinkage, then applied to the outer surface of the small diameter thin or ultra-thin walled base graft.

Specifically, as shown in FIG. 2, the tape-tube may by prepared by initially wrapping 80 the expanded sintered PTFE reinforcement tape around a rigid mandrel in overlapping or otherwise abutting convolutions, to form an elongate, tubular tape configuration. The mandrel-borne tape is then placed in an oven or otherwise heated to a temperature which causes the convolutions of tape to laminate or fuse to one another, thereby forming a tape-tube 82.

Also, the tape-tube may be prepared by the methodology disclosed in U.S. Pat. No. 5,207,960 (Moret de Rocheprise) entitled, METHOD FOR THE MANUFACTURE OF THIN TUBES OF FLUORINATED RESIN, PARTICULARLY OF POLYETRAFLUOROETHYLENE.

iii) Radial Shrinkage of Tape-Tube

The tape-tube is then subjected to radial shrinkage, by any suitable method, including any of the heat-induced or chemical-induced shrinkage methods described herein. Since the tape-tube is devoid of any internal base graft, it may be unnecessary to utilize the gradual or incremental shrinkage described hereabove, as such gradual or incremental shrinkage is primarily intended to avoid puckering or infolding of the base graft. In this regard, the tape tube may simply be placed on a small diameter mandrel, such mandrel having a diameter substantially equal to the intended diameter of the tape-tube after shrinkage thereof. The ends of the tape-tube may be affixed to the mandrel to prevent longitudinal shrinkage or longitudinal shortening of the tape-tube during the shrinkage process. Thereafter, the small diameter mandrel and the tape-tube affixed thereto may be heated to a temperature which causes the tape tube to shrink to the diameter of the mandrel. Thereafter, the tape-tube is removed from the small diameter mandrel and utilized for subsequent fabrication of the desired radially enlargeable tape-reinforced graft.

iv) Fabrication of Tape-Reinforced Graft

The radially enlargeable tape-reinforced graft is fabricated by inserting the previously prepared small diameter tubular base graft into the lumen of the radially shrunken tape-tube 86.

v) Fusion of Tape-Tube to Base Graft

Thereafter, the tape-tube/base graft combination is heated or otherwise treated to cause the tape-tube to fuse to the outer surface of the base graft, 88. Such fusion of the tape-tube to the outer surface of the base graft, results in the formation of the desired radially enlargeable tape-reinforced graft.

In a variation of the above, described alternative method, the reinforcement tape may be longitudinally shrunk, without being formed into a tape-tube as described hereabove. Such longitudinally shrunken tape may then be spirally wrapped around, and laminated to a relatively small diameter base graft—in accordance with the above-described wrapping and lamination methods, thereby forming a radially enlargeable taps-reinforced graft.

3. Method for Endoluminal Placement and In Situ Radial Expansion of the Grafts

The radially enlargeable vascular grafts of the present invention, as discussed hereabove, may be utilized in the manufacture of endovascular grafting systems which are deployable into the lumen of a blood vessel through a catheter or other tubular introducer and subsequently radially expandable such that the lumen of the graft will approximate the lumenal size of the blood vessel wherein the graft is disposed, and the graft will become anchored or affixed to the surrounding blood vessel wall.

It will be appreciated that in many such endovascular applications, it will be desirable to utilize the radially enlargeable tape-reinforced vascular graft of the present invention in conjunction with one or more a) anchoring mechanisms, b) stents or c) other fixation devices, for the purpose of securing and affixing the graft to the surrounding blood vessel wall. Examples of endovascular graft affixation devices, stents and/or other means which may be used for supporting or affixing an endoluminally positioned tubular graft of the present invention are described in the following United States and foreign patents/patent publications: 4,733,665 (Palmaz), 4,776,337 (Palmaz), 5,037,392 (Hillstead), 5,116,318 (Hillstead), 5,135,536 (Hillstead), 5,21,658 (Clouse), 5,219,355 (Parodi et al.), 5,275,622 (Lazarus et al.), 5,282,824 (Gianturco), 5,292,331 (Boneau), 5,330,500 (Song), 5,354,308 (Simon et al), 5,360,443 (Borone et al), 5,015,253 (MacGregor), 5,171,262 (MacGregor), 5,061,275 (Wallsten et al.), 5,282,860 (Matsuno et al.), 5,290,305 (Inoue), 5,304,200 (Spaulding), 5,306,286 (Stack et al.), DT197808 (Choudhury), SU 1217-402-A (Khark), EP 466-518-A (Harrison et al.), EP 579523-A1 (Cottenceau J., et al.), 2,189,150-A (Medinvent), and WO 90/02641 (Bowald et al.).

Also, in endovascular applications wherein it is desired to radially enlarge the graft in situ, it will be appreciated that various types of expansion apparatus may be used to cause the desired radial expansion or radial stretching of the graft. In particular, a generally cylindrical balloon may be formed on the outer surface of a catheter and inserted within the lumen of the shrunken graft during or after placement of the graft within the lumen of the host blood vessel. Thereafter, the balloon may be inflated to cause controlled radial expansion of the graft. After being fully radially enlarged, the graft may be affixed or anchored to the surrounding blood vessel wall.

Figure 3:
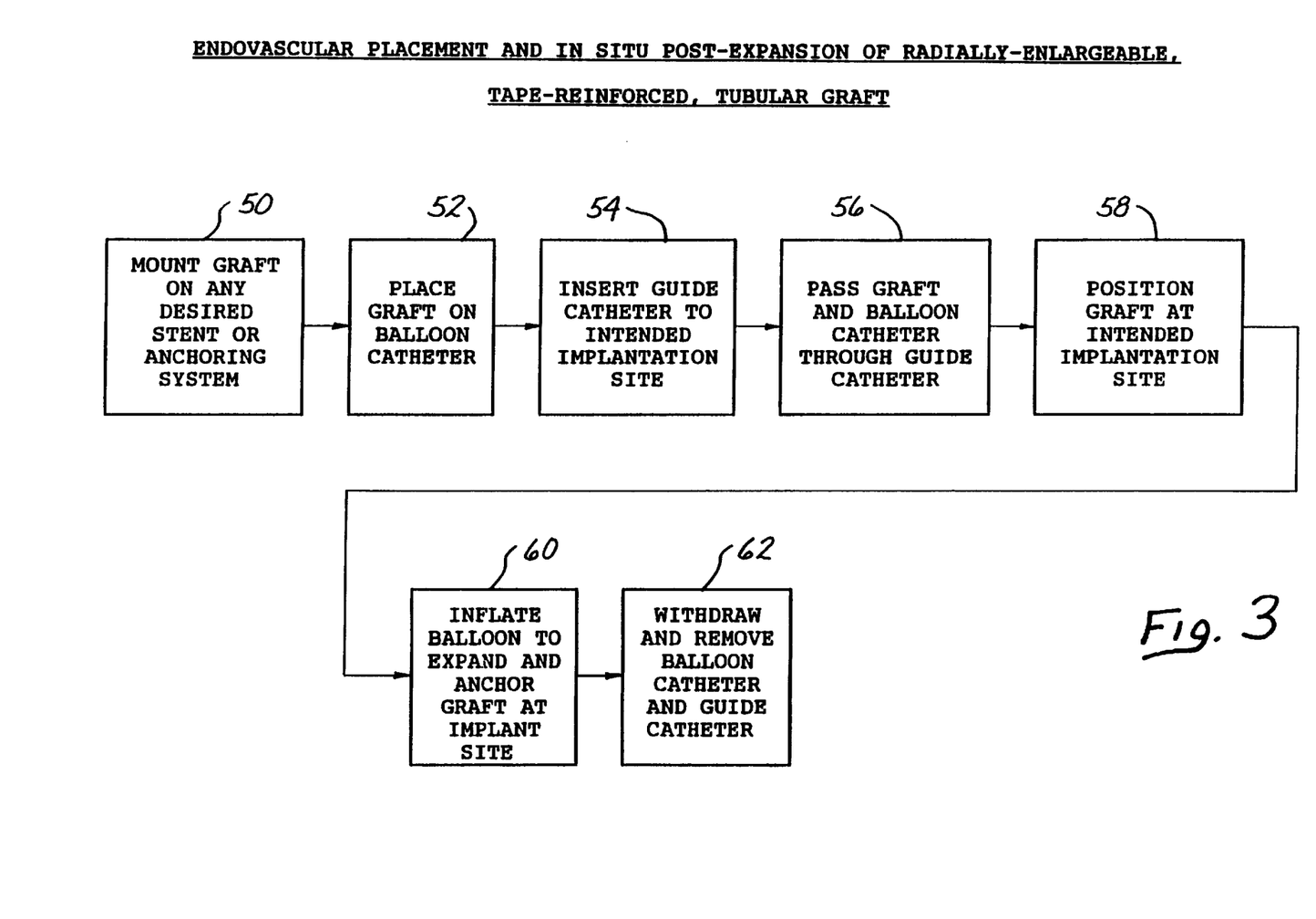
FIG. 3 is a block diagram showing a presently preferred method for endovascular implantation and in situ radial expansion of a tape-reinforced vascular graft of the present invention.

The general preferred method for endovascular placement and in situ post expansion of a radially expandable tape-reinforced tubular PTFE vascular graft of the present invention is shown in FIG. 3.

Initially, the radially enlargeable tape-reinforced tubular vascular graft is mounted on a stent or graft anchoring system 50 to facilitate affixation or anchoring of the graft at its desired location within the lumen of a host blood vessel.

Thereafter, the graft (with the accompanying stent or anchoring system) may be positioned over an inflatable balloon formed on a balloon catheter 52. The balloon will be sized and configured relative to the graft and its accompanying stent or anchoring system, such that subsequent inflation of the balloon will cause the desired radial expansion of the graft. Typically, for standard tubular vascular grafts of generally round cylindrical configuration, a cylindrical balloon configuration will be used.

Thereafter, a guide catheter is inserted 54 into the vasculature and advanced to a point where the distal end of the guide catheter is located adjacent to the intended implantation site. Such guide catheter insertion step 54 may be accomplished percutaneously, as by way of the Seldinger Technique.

The balloon catheter having the graft (with its accompanying stent or anchoring system) positioned thereon is either a) prepositioned within the lumen of the guide catheter and inserted concurrently with the guide catheter insertion 54 or b) advanced through the lumen of the guide catheter after the guide catheter has been inserted 54 and advanced to its desired location within the vasculature. By either method, the balloon catheter (having the graft and its accompanying stent/anchoring apparatus mounted therein) is advanced through the lumen of the guide catheter 56.

The graft (with its accompanying stent or anchoring system) is thus advanced out of the distal end of the guide catheter and is positioned 58 at its intended implantation site within the vasculature.

Thereafter, the balloon is inflated to cause radial expansion 60 the graft at its intended implantation site. Such radial expansion of the graft may also facilitate activation or deployment of the stent or anchoring system such that the expanded graft will become anchored to the surrounding blood vessel wall. In some instances, the anchoring apparatus will consist of piercing members or protrusions which become inserted into the surrounding blood vessel wall as the graft is radially expanded. In other instances, the anchoring system could consist of a stent or other device which frictionally engages the wall of the blood vessel as the graft is radially expanded. Irrespective of the particular type of anchoring system or stent utilized, it is desirable that the act of radially expanding the graft by inflation of the balloon will concurrently actuate the intended anchoring or placement mechanism so as to hold the graft at its intended implantation site.

It will be appreciated that any appropriate radiological or other locating device or apparatus may be used to guide and verify the positioning of the graft at its desired implantation site 58. To facilitate this, the graft may be provided with one or more radial opaque markers to render the graft easily visible by radiographic means. In many applications, it is expected that one or more angioscopes will also be positioned within the blood vessel, adjacent the intended implantation site of the graft, so as to enable the operator to visually guide and verify the positioning 58, expansion 60 and accompanying anchoring of the graft at its intended implantation site.

After the graft has been radially expanded to its desired size and appropriately anchored or implanted at its intended implantation site, the balloon may be deflated and the balloon catheter, as well as the accompanying guide catheter may be withdrawn 62.

By the above-described method, a radially expandable graft of the present invention may be percutaneously, transluminally implanted within a host blood vessel without the need for open surgical excision of the blood vessel.

Although the foregoing has provided a description of a preferred method for transluminal endovascular placement of a radially enlargeable graft of the present invention, it will be appreciated that the grafts of the present invention may also find utility in traditional open surgical implantation methods wherein it is desired to provide a graft having improved strength and improved resistance to suture pull-through. In this regard, radially shrunken endovascular grafts of the present invention may be provided for surgical implantation by traditional open surgical techniques wherein a radially shrunken vascular graft of the present invention is anastomosed into the host blood vessel to replace or bypass a diseased, or damaged segment of the vessel. In this regard, the shrunken size of the graft will be matched to the size of the host blood vessel, and the graft will be sutured in place without effecting any radial enlargement of the graft. The radial shrinkage of the graft which took place during the manufacturing process will have imparted substantial improvements to the overall strength and suture holding properties of the graft, even though no radial enlargement of the graft is effected at the time of implantation.

Although the invention has been described herein with reference to certain preferred embodiments, it will be appreciated that the above-described embodiments may be altered, modified or changed in many different ways without departing from the intended spirit and scope of the invention. For example, the radial shrinkage of the reinforcement tape, or of the entire tape-reinforced tubular graft, may be accomplished by any suitable method other than the heat-induced shrinkage methods described specifically herein, including the use of any suitable chemical shrinkage technique whereby exposure of the reinforcement tape and/or the entire tape-reinforced graft to a particular chemical will cause the reinforcement tape and/or the entire tape-reinforced graft to undergo the desired radial shrinkage. It is intended that all such modifications changes or alterations to the above-described methods be included within the scope of the following claims.

What is claimed is:

1. In a process for manufacturing a radially enlargeable tubular vascular graft having a taped reinforcement layer, which includes the step of providing a workpiece comprising a tubular base graft having an outer surface and a hollow lumen extending longitudinally therethrough, the tubular base graft being formed substantially of a sintered fluoropolymer material and the outer surface having a first diameter after sintering, wherein the process further comprises the improvement of:

a longitudinally restraining the workpiece; and a radially shrinking the workpiece by heating, thereby causing the tubular base graft to assume a radially shrunken state with its outer surface having a second diameter which is smaller than the first diameter, and from which the tubular base graft may be subsequently radially enlarged to return to the first diameter.

2. The process of claim 1 wherein step (b) comprises:

initially radially shrinking the workpiece by a first incremental amount; and, subsequently radially shrinking the workpiece by at least one additional incremental amount.

3. The process of claim 2 wherein said step of subsequently radially shrinking the workpiece by at least one additional incremental amount further comprises:

radially shrinking the workpiece by a second incremental amount.

4. The process of claim 3 wherein step (b) further comprises:

subsequently radially shrinking the workpiece by a third incremental amount.

5. The process of claim 4 wherein step (b) further comprises:

subsequently radially shrinking the workpiece by a fourth incremental amount.

6. The process of claim 5 wherein step (b) further comprises:

subsequently radially shrinking the workpiece by a fifth incremental amount.

7. The process of claim 1 wherein the lumen of the tubular base graft of the workpiece provided in step (a) has a first lumenal diameter prior to undergoing radial shrinkage in step (b) of the process, and wherein step (b) of the process comprises:

providing a first shrinkage mandrel having an outer diameter which is smaller than the lumenal diameter of the graft;

inserting said first shrinkage mandrel into the lumen of the workpiece;

heating the workpiece to cause the workpiece to radially shrink until the lumenal diameter of the workpiece is substantially the same as the outer diameter of said first shrinkage mandrel.

8. The process of claim 7 wherein step (b) of said process further comprises:

removing said first shrinkage mandrel from the lumen of the workpiece;

providing a second shrinkage mandrel having an outer diameter which is smaller than the outer diameter of said first shrinkage mandrel;

inserting said second shrinkage mandrel into the lumen of the workpiece; and, heating the workpiece to cause the workpiece to radially shrink until the lumenal diameter of the workpiece is substantially the same as the outer diameter of the second shrinkage mandrel.

9. The process of claim 8 wherein step (b) of said process further comprises:

removing said second shrinkage mandrel from the lumen of the workpiece;

providing a third shrinkage mandrel having an outer diameter which is smaller than the outer diameter of said second shrinkage mandrel;

inserting said third shrinkage mandrel into the lumen of the workpiece; and, heating the workpiece to cause the workpiece to radially shrink until the lumenal diameter of the workpiece is substantially the same as the outer diameter of the third shrinkage mandrel.

10. The process of claim 9, wherein step (b) further comprises:

removing said third shrinkage mandrel from the lumen of the workpiece:

providing a fourth shrinkage mandrel having an outer diameter which is smaller than the outer diameter of the third shrinkage mandrel;

inserting said fourth shrinkage mandrel into the lumen of the workpiece and, heating the workpiece to cause the workpiece to radially shrink until the lumenal diameter of the workpiece is substantially the same as the outer diameter of the fourth shrinkage mandrel.

11. The process of claim 10 wherein step (b) further comprises:

removing the fourth shrinkage mandrel from the lumen of the workpiece;

providing a fifth shrinkage mandrel having an outer diameter which is smaller than the outer diameter of the fourth shrinkage mandrel;

inserting said fifth shrinkage mandrel into the lumen of the workpiece; and, heating the workpiece to cause the workpiece to radially shrink until the lumenal diameter of the workpiece is substantially the same as the outer diameter of the fifth shrinkage mandrel.

12. The process of claim 1 wherein the tubular base graft of the workpiece is formed of expanded, sintered PTFE.

13. The process of claim 1 wherein step (b) comprises:

radially shrinking said workpiece so that the radial dimension of the workpiece is decreased by more than 5%.

14. The process of claim 1 wherein step (b) comprises:

radially shrinking said workpiece such that the radial dimension of said workpiece is decreased by more than 10%.

15. The process of claim 1 wherein step (b) comprises:

radially shrinking said workpiece such that the radial dimension of said workpiece is decreased by more than 20%.

16. The process of claim 1 wherein step (b) comprises:

radially shrinking said workpiece such that the radial dimension of said workpiece is decreased by more than 40%.

17. The process of claim 1, further comprising the step of wrapping a sintered monofilament bead about the workpiece.

18. The process of claim 1 wherein the reinforcement tape of the workpiece is formed substantially of expanded, sintered PTFE.

19. A process for manufacturing a radially expandable tubular vascular graft having a tape reinforcement layer consisting essentially of sintered PTFE, the process comprising the steps of:

a. providing a tubular base graft formed of expanded PTFE, said tube having a first end, a second end, an outer surface, and a lumen extending longitudinally therethrough and having a first lumenal diameter;

b. sintering the tubular base graft;

c. inserting a first rigid mandrel into the lumen of the tubular base graft, the first rigid mandrel having an outer diameter which is substantially equal to the first lumenal diameter of the tubular base graft;

d. heating the base graft to a temperature above 327 deg. C.;

e. removing the first mandrel from the lumen of the graft;

f. inserting a second rigid mandrel into the lumen of the graft, the second rigid mandrel having an outer diameter which is smaller than the first lumenal diameter of the lumen of the graft:

g. longitudinally restraining the graft;

h. again heating the graft to a temperature sufficient to cause the graft to shrink radially until its lumenal diameter is substantially the same as the outer diameter of the second rigid mandrel, and from which the graft may be subsequently radially enlarged to return the lumenal diameter of the graft to the first lumenal diameter.

20. The process of claim 19, wherein step (f) further comprises affixing the ends of the graft to the first mandrel to prevent longitudinal shortening of the graft during subsequent heating thereof in step (g).

21. The process of claim 20, further comprising the step of wrapping a sintered monofilament bead about the graft.

22. The process of claim 21, further comprising the steps of:

i. removing the second rigid mandrel from the lumen of the graft;

j. inserting a third rigid mandrel into the lumen of the graft, the third rigid mandrel having an outer diameter which is smaller than the outer diameter of second rigid mandrel;

k. again heating the graft to a temperature sufficient to cause further radial shrinkage of the graft until the lumenal diameter of the graft is substantially the same as the outer diameter of the third rigid mandrel.

23. The process of claim 22 wherein step (m) further comprises fixing the ends of the graft to the third rigid mandrel to prevent longitudinal shortening of the graft during subsequent heating in step (k).

24. The process of claim 22 further comprising the steps of:
  l. removing the third rigid mandrel from the lumen of the graft;
  m. inserting a fourth rigid mandrel into the lumen of the graft, the fourth rigid mandrel having an outer diameter which is smaller than the outer diameter of the third rigid mandrel;
  n. again heating the graft to a temperature sufficient to cause further radial shrinkage of the graft until its lumenal diameter is substantially the same as the outer diameter of the fourth rigid mandrel.

25. The process of claim 24 further comprising the steps of:
  o. removing the fourth rigid mandrel from the lumen of the graft;
  p. inserting a fifth rigid mandrel into the lumen of the graft, the fifth rigid mandrel having an outer diameter which is smaller than the outer diameter of the fourth rigid mandrel;
  q. again heating the graft to a temperature sufficiently to effect further radial shrinkage of the graft until its lumenal diameter is substantially the same as the outer diameter of the fifth rigid mandrel.

* * * * *